(12) United States Patent
von Hagen et al.

(10) Patent No.: US 7,470,778 B2
(45) Date of Patent: Dec. 30, 2008

(54) USE OF IONIC LIQUIDS FOR PROTEIN EXTRACTION

(75) Inventors: Jeorg von Hagen, Griesheim (DE); Uwe Michelsen, Weinheim (DE)

(73) Assignee: Merck Patent GmbH, Darmstadt (DE)

( * ) Notice: Subject to any disclaimer, the term of this patent is extended or adjusted under 35 U.S.C. 154(b) by 67 days.

(21) Appl. No.: 11/450,889

(22) Filed: Jun. 12, 2006

(65) Prior Publication Data
US 2007/0026460 A1    Feb. 1, 2007

(30) Foreign Application Priority Data
Jun. 13, 2005   (DE) .................. 10 2005 027 172

(51) Int. Cl.
*A23J 1/00* (2006.01)
*C07K 17/00* (2006.01)

(52) U.S. Cl. .................. 530/412; 530/422

(58) Field of Classification Search ............ 204/468; 540/541
See application file for complete search history.

(56) References Cited

U.S. PATENT DOCUMENTS
2006/0149035 A1   7/2006  Rudolph et al.

FOREIGN PATENT DOCUMENTS
DE       10240098 A1    3/2004
WO       WO 2004/024279 A    3/2004
WO       WO 2004/080579 A2   9/2004
WO       WO 2004/086001 A1  10/2004
WO       WO 2005/103070 A   11/2005

OTHER PUBLICATIONS

Shimojo, K., et al. 2006 Biomacromolecules 7(1): 2-5, (plus chart 1).*
Jain, N. et al., "Chemical and biochemical transformations in ionic liquids," Tetrahedron, vol. 61 No. 5, Jan. 31, 2005, Elsevier Science Publishers, Amsterdam, NL, pp. 1015-1060.
Yang, Z. et al., "Ionic liquids: Green solvents for nonaqueous biocatalysis," Enzyme and Microbial Technology, vol. 37 No. 1, Jun. 1, 2005, Stoneham, MA, USA, pp. 19-28.

* cited by examiner

*Primary Examiner*—Maryam Monshipouri
*Assistant Examiner*—Marsha M Tsay
(74) *Attorney, Agent, or Firm*—Millen, White, Zelano, Branigan, P.C.

(57) ABSTRACT

The present invention relates to a method for the extraction of proteins, protein fragments and/or peptides from biological samples, where the extractants employed are ionic liquids of the general formula $K^+A^-$, to a kit for the extraction of proteins, protein fragments and/or peptides, and to the use thereof.

8 Claims, No Drawings

USE OF IONIC LIQUIDS FOR PROTEIN EXTRACTION

This application claims foreign priority of German application no. 102005027172.3, filed on Jun. 13, 2005.

The present invention relates to a method for the extraction of proteins, protein fragments and/or peptides from biological samples, where the extractants employed are ionic liquids of the general formula $K^+A^-$, to a kit for the extraction of proteins, protein fragments and/or peptides, and to the use thereof.

The detection or analysis of proteins is increasing in importance in medicine. This applies in particular to the analysis of tissue samples in order to ascertain signs of a disease or evidence of a pathological change. For this purpose, analyses of the complete proteome of the cell are investigated. To this end, it is essential to extract all proteins of a given sample quantitatively, since only analysis of all proteins involved in their entirety allows conclusions to be drawn on diseases and the genesis thereof.

The object was therefore to provide methods with the aid of which proteins can be extracted from biological samples to enable them to be analyzed further.

The present invention accordingly relates to methods for the extraction of proteins, protein fragments and/or peptides from biological samples, where the extractants employed are ionic liquids of the general formula $K^+A^-$.

Ionic liquids or liquid salts are ionic species which consist of an organic cation and a generally inorganic anion. They do not comprise neutral molecules and usually have melting points below 373 K.

Intensive research is currently being carried out in the area of ionic liquids since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—New Solutions for Transition-Metal Catalysis], *Angew Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

Surprisingly, it has been found that ionic liquids of the general formula $K^+A^-$ are suitable for the extraction of proteins, protein fragments and/or peptides from biological samples. This also applies if the biological samples have been fixed, as is usually the case in sample preparation of biological samples. Surprisingly, the extraction method according to the invention can also be used for fixed samples, which expands the potential uses of the methods enormously. In this way, biological samples can be treated universally by the methods according to the invention in order to extract proteins, protein fragments and/or peptides therefrom. The method according to the invention has the advantage that the constituents to be extracted are not degraded, i.e. their chemical constitution is retained. This is a significant advantage over known methods, as described, for example, in WO 2004/080579, in which the proteins to be extracted have to be degraded to peptides in a proteolytic step in order to enable subsequent analysis. Overall, the method according to the invention thus enables simple preparation of biological samples for the isolation of proteins, protein fragments and/or peptides which was not accessible using the method described from the prior art.

In the methods according to the invention, proteins, protein fragments and/or peptides can be extracted from all biological samples known to the person skilled in the art. The biological samples are preferably tissues, such as, for example, biopsies and histological preparations, cells, cell cultures and/or body fluids, such as, for example, blood, plasma, serum, urine, liquor or saliva. The extraction of proteins from tissues and cell cultures allows, in particular, the detection of specific proteins, for example the detection of proteins which indicate the presence of diseases. The method according to the invention is therefore also particularly advantageous for pathologically interesting tissue samples.

The biological samples may be unfixed or fixed, preferably fixed. The fixing may have been carried out by all methods known to the person skilled in the art, for example through the use of formalin, glutaraldehyde, formalin substitutes, alcohols, such as, for example, ethanol, methanol or isopropanol, or inert materials, such as, for example, paraffin, resins or polymers.

The biological samples are preferably fixed using formalin. Formalin is the most common fixing agent in the preparation of histological samples and, owing to the low price and good fixing action, is employed widely and has now been used for more than one hundred years. However, fixing using formalin has the disadvantage that crosslinking of the proteins with the sample matrix occurs. The proteins consequently generally become insoluble and are not available for further analysis. Through the use of ionic liquids in the methods according to the invention, however, the proteins can also be extracted from these samples with retention of their structure and then analyzed further. In this way, the commonest fixing method using formalin is expanded in its practicability without limiting the possibilities of subsequent analysis. It is thus now also possible using the methods according to the invention to investigate samples which have already been preserved for a very long time by means of the use of formalin using modern protein analysis, i.e. there is no time limit to the ability of samples to be analyzed.

All ionic liquids of the general formula $K^+A^-$ known to the person skilled in the art, for example with hexafluorophosphate, tetrafluoroborate or halide anions, are suitable in the methods according to the invention. Examples of suitable ionic liquids are trihexyl(tetradecyl)phosphonium hexafluorophosphate, trihexyl(tetradecyl)phosphonium chloride and trihexyl(tetradecyl)phosphonium tetrafluoroborate.

The anion $A^-$ of the ionic liquid is preferably selected from the group of the imides, in particular those of the general formula $$[N(R_f)_2]^{31}$$ 

where $R_f$ denotes partially or fully fluorine-substituted alkyl having 1 to 8 C atoms or $R_{f2}X$, where $R_{f2}$ denotes partially or fully fluorine-substituted alkyl having 1 to 8 C atoms and X denotes $SO_2$ or CO, from the group of the fluoroalkylphosphates, in particular those of the general formula $$[PF_x(C_yF_{2y+1-z}H_z)_{6-x}]^-$$ 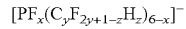

where $1 \leq x < 6$, $1 \leq y \leq 8$ and $0 \leq z \leq 2y+1$, or mixtures thereof.

$R_f$ is preferably trifluoromethyl, pentafluoroethyl, nonafluorobutyl or $R_{f2}SO_2$, in particular trifluoromethyl or $R_{f2}SO_2$, where $R_{f2}$ is particularly preferably trifluoromethyl. In the case of the fluoroalkylphosphates, preferably x=3, z=0 and y=2, 3 or 4, where y is very particularly preferably=2.

Ionic liquids containing the particularly preferred [(CF$_3$SO$_2$)$_2$N]$^-$ or [PF$_3$(C$_2$F$_5$)$_3$]$^-$ anions are particularly suitable for the extraction of proteins, protein fragments and/or peptides in the methods according to the invention.

There are no restrictions per se with respect to the choice of the cation K$^+$ of the ionic liquid. However, preference is given to organic cations, particularly preferably ammonium, phosphonium, uronium, thiouronium, guanidinium or heterocyclic cations.

Ammonium cations can be described, for example, by the formula (1)

where
R in each case, independently of one another, denotes H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms which may be substituted by alkyl groups having 1-6 C atoms,
in which one or more R may be partially or fully substituted by halogens, in particular —F and/or —Cl, or R may be partially substituted by —OH, —OR', —CN, —C(O)OH, —C(O)NR'$_2$, —SO$_2$NR'$_2$, —C(O)X, —SO$_2$OH, —SO$_2$X or —NO$_2$,
one or two non-adjacent carbon atoms of the R which are not in the α-position, i.e. adjacent to N, may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—,
R' may be=H, non-, partially or perfluorinated C$_1$- to C$_6$-alkyl, C$_3$- to C$_7$-cycloalkyl, or unsubstituted or substituted phenyl,
X=halogen,
or R may be OR', or NR'$_2$, with the proviso that at most one substituent R in the formula (1) is OR' or NR'$_2$.

Phosphonium cations can be described, for example, by the formula (2)

[PR$^2_4$]$^+$ (2), where
R$^2$ in each case, independently of one another, denotes H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms which may be substituted by alkyl groups having 1-6 C atoms,
in which one or more R$^2$ may be partially or fully substituted by halogens, in particular —F and/or —Cl, or R$^2$ may be partially substituted by —OH, —OR', —CN, —C(O)OH, —C(O)NR'$_2$, —SO$_2$NR'$_2$, —C(O)X, —SO$_2$OH, —SO$_2$X or —NO$_2$,
one or two non-adjacent carbon atoms of the R$^2$ which are not in the α-position, i.e. adjacent to P, may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—,
R'=H, non-, partially or perfluorinated C$_1$- to C$_6$-alkyl, C$_3$- to C$_7$-cycloalkyl, or unsubstituted or substituted phenyl,
X=halogen,
or R$^2$ may be OR', NR'$_2$.

However, cations of the formulae (1) and (2) in which all four or three substituents R and R$^2$ are fully substituted by halogens are excluded, for example the tris(trifluoromethyl)methylammonium cation, the tetra(trifluoromethyl)ammonium cation or the tetra(nonafluorobutyl)ammonium cation.

Uronium cations can be described, for example, by the formula (3)

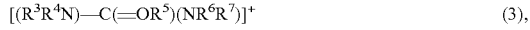

and thiouronium cations can be described by the formula (4)

where
R$^3$ to R$^7$ each, independently of one another, denote hydrogen, where hydrogen is excluded for R$^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms which may be substituted by alkyl groups having 1-6 C atoms,
in which one or more of the substituents R$^3$ to R$^7$ may be partially or fully substituted by halogens, in particular —F and/or —Cl, or R$^3$ to R$^7$ may be partially substituted by —OH, —OR', —CN, —C(O)OH, —C(O)NR'$_2$, —SO$_2$NR'$_2$, —C(O)X, —SO$_2$OH, —SO$_2$X or —NO$_2$,
one or two non-adjacent carbon atoms of R$^3$ to R$^7$ which are not in the α-position, i.e. adjacent to N, may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—,
R'=H, non-, partially or perfluorinated C$_1$- to C$_6$-alkyl, C$_3$- to C$_7$-cycloalkyl, or unsubstituted or substituted phenyl, and
X=halogen.

Guanidinium cations can be described by the formula (5)

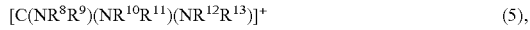

where
R$^8$ to R$^{13}$ each, independently of one another, denote hydrogen,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
in which substituents R$^8$ to R$^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X or —NO$_2$,
one or two non-adjacent carbon atoms of R$^8$ to R$^{13}$ which are not in the α-position, i.e. adjacent to N, may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, R'=H, non-, partially or perfluorinated C$_1$- to C$_6$-alkyl, C$_3$- to C$_7$-cycloalkyl, or unsubstituted or substituted phenyl, X=halogen, or R$^8$ to R$^{13}$ may be —CN, NR'$_2$, —OR'.

In addition, it is possible to employ cations of the general formula (6)

$$[HetN]^+ \qquad (6),$$

where

HetN$^+$ denotes a heterocyclic cation selected from the group

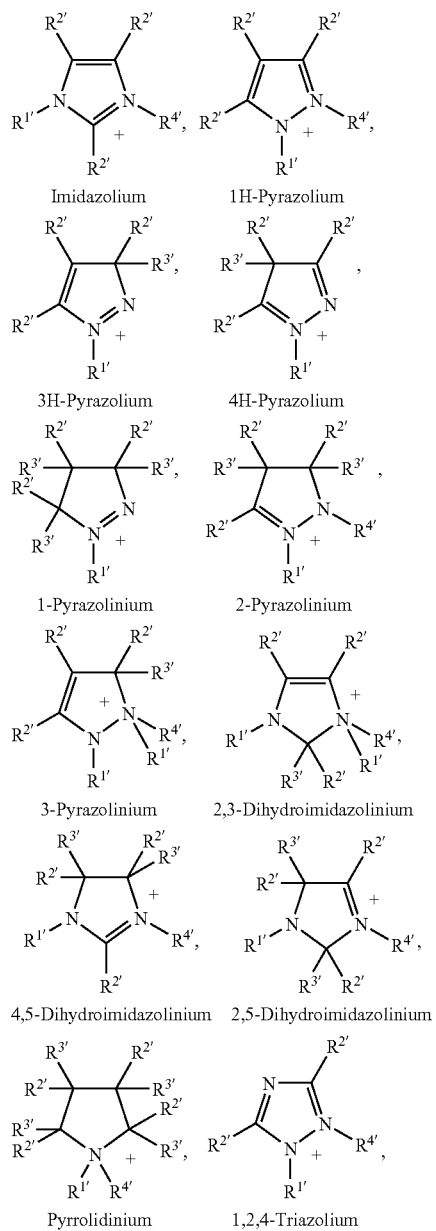

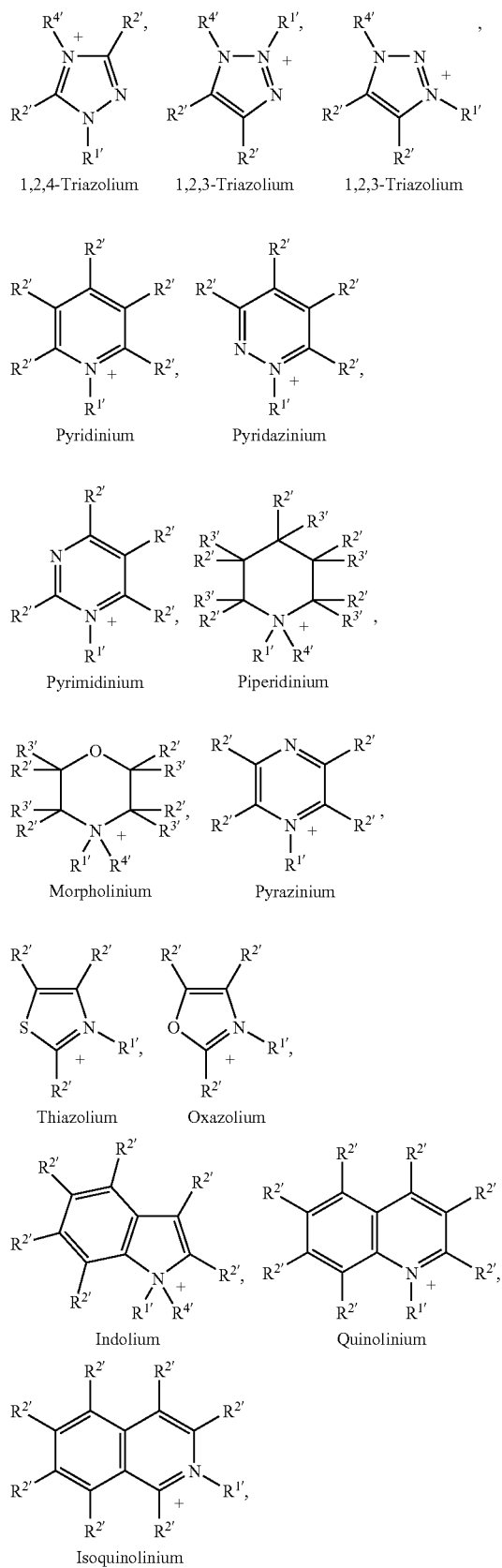

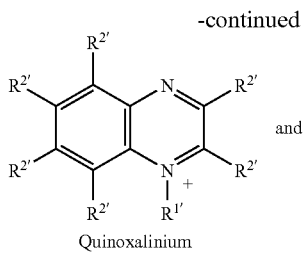

Quinoxalinium

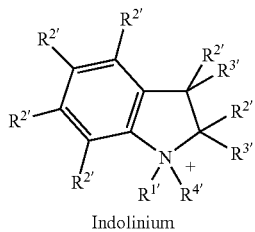

Indolinium where the substituents
$R^{1'}$ to $R^{4'}$ each, independently of one another, denote hydrogen,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms which may be substituted by alkyl groups having 1-6 C atoms,
saturated, partially or fully unsaturated heteroaryl, heteroaryl-$C_1$-$C_6$-alkyl or aryl-$C_1$-$C_6$-alkyl,
in which substituents $R^{1'}$ to $R^{4'}$ may be partially or fully substituted by halogens, in particular —F and/or —Cl, or —OH, —OR', —CN, —C(O)OH, —C(O)NR'$_2$, —SO$_2$NR'$_2$, —C(O)X, —SO$_2$OH, —SO$_2$X or —NO$_2$, but where $R^{1'}$ and $R^{4'}$ cannot simultaneously be fully substituted by halogens,
one or two non-adjacent carbon atoms of the substituents $R^{1'}$ to $R^{4'}$ which are not bonded to the heteroatom may be replaced by atoms and/or atom groups selected from —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—,
R'=H, non-, partially or perfluorinated $C_1$- to $C_6$-alkyl, $C_3$- to $C_7$-cycloalkyl, or unsubstituted or substituted phenyl,
X=halogen,
and the substituents $R^{1'}$, $R^{2'}$, $R^{3'}$ and/or $R^{4'}$ together may also form a ring system, or may be —CN, —OR', —NR'$_2$, —P(O)R'$_2$, —P(O)(OR')$_2$, —P(O)(NR'$_2$)$_2$, —C(O)R', —C(O)OR'.

For the purposes of the present invention, fully unsaturated substituents are also taken to mean aromatic substituents.

In accordance with the invention, suitable substituents R and $R^2$ to $R^{13}$ of the compounds of the formulae (1) to (5), besides hydrogen, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, isopropyl, propyl, butyl, sec-butyl, tert-butyl, pentyl, hexyl, octyl, decyl or tetra-decyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

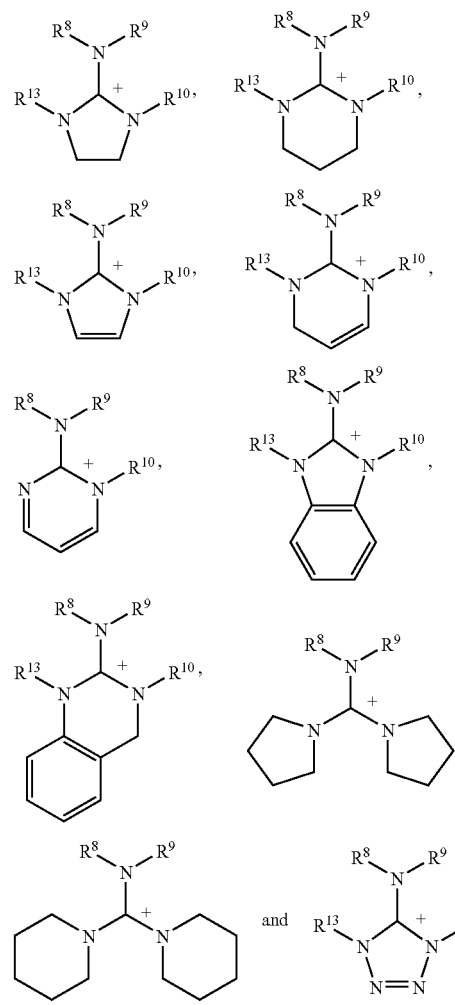

where the substituents $R^8$ to $R^{10}$ and $R^{13}$ can have a meaning or particularly preferred meaning indicated above.

If desired, the carbocyclic or heterocyclic rings of the guanidinium cations indicated above may also be substituted by $C_1$- to $C_6$-alkyl, $C_1$- to $C_6$-alkenyl, NO$_2$, F, Cl, Br, I, OH, $C_1$-$C_6$-alkoxy, SCF$_3$, SO$_2$CF$_3$, COOH, SO$_2$NR'$_2$, SO$_2$X' or SO$_3$H, where X and R' have a meaning indicated above, substituted or unsubstituted phenyl or an unsubstituted or substituted heterocycle.

Up to four substituents of the uronium cation $[(R^3R^4N)—C(=OR^5)(NR^6R^7)]^+$ or thiouronium cation $[(R^3R^4N)—C(=SR^5)(NR^6R^7)]^+$ may also be bonded in pairs in such a way that mono-, bi- or polycyclic cations are formed.

Without restricting generality, examples of such cations are indicated below, where Y=O or S:

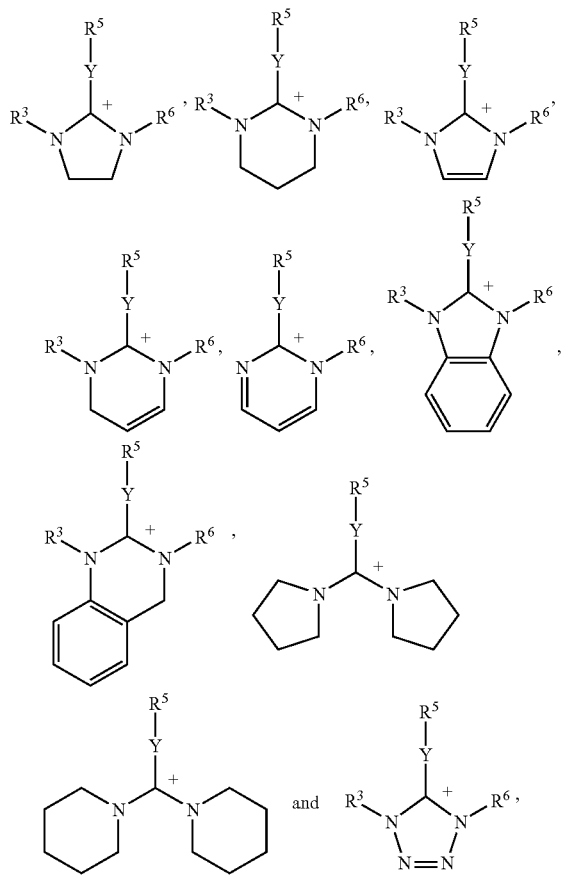

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR'_2$, $SO_2X$ or $SO_3H$ or substituted or unsubstituted phenyl or an unsubstituted or substituted heterocycle, where X and R' have a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (5) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (6), besides hydrogen, are preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl, optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, $—C_9H_{17}$, $—C_{10}H_{19}$ to $—C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, $—C_9H_{15}$, $—C_{10}H_{17}$ to $—C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —CN, —C(O)OH, —C(O)NR'$_2$, —SO$_2$NR'$_2$, —C(O)X, —SO$_2$OH, —SO$_2$X, —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— and —P(O)R'—, where R'=non-, partially or perfluorinated $_1$- to $C_6$-alkyl, $C_3$- to $C_7$-cycloalkyl, or unsubstituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—

$C_4H_9$, $-CF_3$, $-C_2F_5$, $-C_3F_7$, $-C_4F_9$, $-C(CF_3)_3$, $-CF_2SO_2CF_3$, $-C_2F_4N(C_2F_5)C_2F_5$, $-CHF_2$, $-CH_2CF_3$, $-C_2F_2H_3$, $-C_3FH_6$, $-CH_2C_3F_7$, $-C(CFH_2)_3$, $-CH_2C(O)OH$, $-CH_2C_6H_5$, $-C(O)C_6H_5$ or $P(O)(C_2H_5)_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' denotes F, Cl or Br, and R" denotes a non-, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m- or p-(trifluoromethyl)phenyl, o-, m- or p-(trifluoromethoxy)phenyl, o-, m- or p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, 4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-,3-, 4-, 5-, 6- or 7-benzopyrazolyl, 2-, 4-, 5-, 6- or 7-benzoxazolyl, 3-, 4-, 5-, 6- or 7-benzothiazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl or pyridinylhexyl, where the heterocycles described above may furthermore be linked to the alkylene chain in this way.

$HetN^+$ is preferably

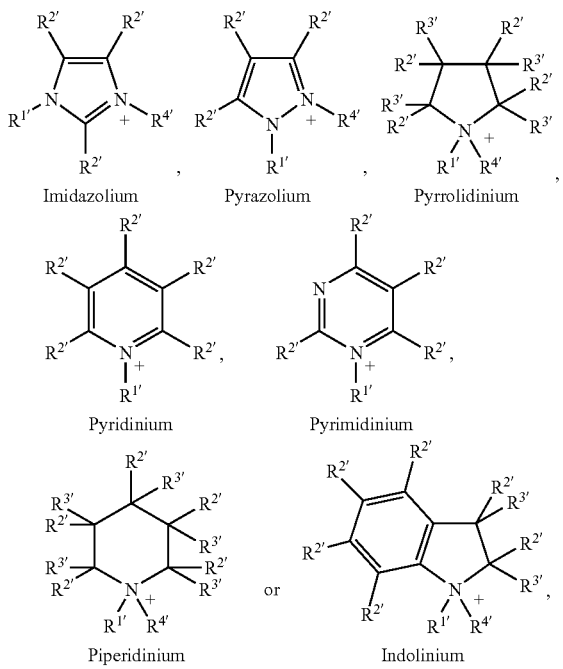

Imidazolium, Pyrazolium, Pyrrolidinium, Pyridinium, Pyrimidinium, Piperidinium or Indolinium, where the substituents $R^{1'}$ to $R^{4'}$ each, independently of one another, have a meaning described above.

The cations of the ionic liquid according to the invention are preferably ammonium, phosphonium, imidazolium, pyridinium or pyrrolidinium cations.

Very particular preference is given to the use for the extraction in the methods according to the invention of ammonium, phosphonium, imidazolium, pyridinium or pyrrolidinium trifluoromethylsulfonylimides or ammonium or phosphonium tris(pentafluoroethyl)trifluorophosphates, where trihexyl(tetradecyl)phosphonium hexafluorophosphate, trihexyl(tetradecyl)phosphonium chloride, trihexyl(tetradecyl)phosphonium tetrafluoroborate, N-(3-hydroxypropyl)-N-methylpyrrolidinium bis(trifluoromethylsulfonyl)imide, N-(ethoxymethyl)-N-methylpyrrolidinium bis(trifluoromethylsulfonyl)imide, N-(2-methoxyethyl)-N-methylpyrrolidinium bis(trifluoromethylsulfonyl)imide, N-(2-methoxyethyl)pyridinium bis(trifluoromethylsulfonyl)imide, N-ethyl-4-(N,N-dimethylammonium)pyridinium bis(trifluoromethylsulfonyl)imide, N-butyl4-(N,N-dimethylammonium)pyridinium bis(trifluoromethylsulfonyl)imide, N-hexyl4-(N,N-dimethylammonium)pyridinium bis(trifluoromethylsulfonyl)imide, 1-(3-hydroxypropyl)-3-methylimidazolium bis(trifluoromethylsulfonyl)imide, 1-(ethoxymethyl)-3-methylimidazolium bis(trifluoromethylsulfonyl)imide, 1-(2-methoxyethyl)-3-methylimidazolium bis(trifluoromethylsulfonyl)imide, 1-(2-ethoxyethyl)-3-methylimidazolium bis(trifluoromethylsulfonyl)imide, tetrabutylammonium bis(trifluoromethylsulfonyl)imide, tetraethylammonium bis(trifluoromethylsulfonyl)imide, trihexyl(tetradecyl)ammonium trifluoromethylsulfonylimide, methyltrioctylammonium bis(trifluoromethylsulfonyl)imide, (ethoxymethyl)ethyidimethylammonium bis(trifluoromethylsulfonyl)imide, (2-ethoxymethyl)ethyldimethylammonium bis(trifluoromethylsulfonyl)imide, (2-ethoxyethyl)ethyldiethylammonium bis(trifluoromethylsulfonyl)imide, ethyldimethylpropylammonium bis(trifluoromethylsulfonyl)imide, trihexyl(tetradecyl)phosphonium bis(trifluoromethylsulfonyl)imide, trihexyl(tetradecyl)phosphonium tris (pentafluoroethyl)trifluorophosphate, tetrabutylphosphonium tris(pentafluoroethyl)trifluorophosphate, tetramethylammonium tris(pentafluoroethyl)trifluorophosphate, tetraethylammonium tris(pentafluoroethyl)trifluorophosphate or tetrabutylammonium tris(pentafluoroethyl)trifluorophosphate, and particularly preferably N-(3-hydroxypropyl)-N-methylpyrrolidinium bis(trifluoromethylsulfonyl)imide, N-(ethoxymethyl)-N-methylpyrrolidinium bis(trifluoromethylsulfonyl)imide, trihexyl(tetradecyl)ammonium trifluoromethylsulfonylimide, trihexyl(tetradecyl)phosphonium trifluoromethylsulfonylimide or tetrabutylammonium tris(pentafluoroethyl)trifluorophosphate, give particularly good results in the methods according to the invention.

The methods according to the invention can be carried out at temperatures of 0 to 95° C., preferably at 55 to 65° C. and very particularly preferably at 60° C. At the preferred temperatures, improved extraction in a relatively short time is observed. For gentle extraction, in particular of relatively sensitive proteins, protein fragments and/or peptides, it is advisable to carry out the method according to the invention at lower temperatures within the stated temperature range, taking into account a longer extraction time which will be necessary for this purpose.

The methods according to the invention are suitable for the extraction of proteins, protein fragments and/or peptides from biological samples with retention of the cellular basic structure of the samples. In addition, however, it is also conceivable to use the methods according to the invention for correspondingly pretreated samples, in which, for example, the cellular basic structure has been destroyed before use of the methods according to the invention. This pretreatment can be carried out in all ways known to the person skilled in the art, for example by manual homogenization or by vortexing.

The extracts obtained with the aid of the methods according to the invention comprise proteins, protein fragments and/or peptides. These are suitable for all types of protein analysis known to the person skilled in the art, for example electrophoresis (for example two-dimensional gel electrophoresis), immunochemical detection methods (for example western blot analysis, ELISA, RIA), protein arrays (for example planar and bead-based systems), mass spectrometry (for example Maldi, Esi and Seldi) and all biochromatographic separation methods (IEX, SEC, HIC and affinity chromatography).

The present invention likewise relates to a kit for the extraction of proteins, protein fragments and/or peptides by one of the methods according to the invention described above, comprising at least one ionic liquid. The kit according to the invention may comprise one or more ionic liquids. If the kit comprises more than one ionic liquid, these may be in separate form or together in the form of a mixture. The above-mentioned and particularly preferred ionic liquids are preferably present in the kit.

In addition, the kit may, in a further embodiment, additionally comprise at least one reagent which is suitable for the precipitation of proteins, protein fragments and/or peptides, where the reagent can be selected from all precipitation reagents known to the person skilled in the art, for example trichloroacetic acid.

The kit according to the invention enables the user to extract proteins from biological samples in a simple manner and, if desired, also to precipitate them for use in further analysis.

The present invention likewise relates to the use of the kits according to the invention for the extraction of proteins, protein fragments and/or peptides from biological samples.

Even without further comments, it is assumed that a person skilled in the art will be able to utilize the above description in the broadest scope. The preferred embodiments and examples should therefore merely be regarded as descriptive disclosure which is absolutely not limiting in any way.

Without further elaboration, it Is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the forgoing and in the following examples, all temperatures are set forth uncorrected in degrees Celsius and, all parts and percentages are by weight, unless otherwise indicated.

EXAMPLES

Example 1

1 g of a formalin-fixed tissue sample (for example lung, heart, kidney, liver, spleen) is washed a number of times with 10 ml of isotonic phosphate-buffered saline solution and cut into small pieces using a scalpel. 0.1 g of the cut-up sample is mixed with 60 µl of trihexyl(tetradecyl)phosphonium trifluoromethylsulfonylimide and incubated at 60° C. over a period of two hours in a rotary mixer. The supernatant solution is separated off and can be employed for further analysis of the proteins present therein.

Protein Analysis

An SDS-polyacrylamide gel electrophoresis is carried out as follows with the extract obtained in Example 1: 3 µl of the protein extract are mixed with 16 µl of SDS sample application buffer (3M Tris pH 8.5, 24% of glycerol (v/v), 8% of sodium dodecylsulfate (w/v), 2% of 2-mercaptoethanol, 0.1% of Bromophenol Blue (w/v)), and the mixture is incubated at 95° C. for 5 minutes. After centrifugation at 10,000× g, the sample is applied to a 10% SDS-PAGE and separated for 90 minutes at 120 volts.

For identification of the extracted proteins, a Western Blot of the gel is carried out using antibodies, for example against the membrane protein calnexin (90 kDa, anticalnexin, C-terminal, 1:2000, Calbiochem Cat. No.: 208880). In the Western Blot analysis, calnexin is identified in its native molecular size.

Overall, it is found that the methods according to the invention are advantageously suitable for the extraction of proteins from biological samples.

The entire disclosure of all applications, patents and publications, cited herein and of corresponding German Application No. 10 2005 027 172.3, filed Jun. 13, 2005 is incorporated by reference herein.

The preceding examples can be repeated with similar success by substituting the generically or specifically described reactants and/or operating conditions of this invention for those used in the preceding examples.

We claim:

1. A method for extraction of proteins, protein fragments and/or peptides from a biological sample, comprising treating said biological sample with an extractant, wherein the extractant employed is an ionic liquid of the formula $K^+A^-$, wherein $K^+$ is a cation selected from the group consisting of ammonium, phosphonium, uronium, thiouronium, guanidinium or a heterocyclic cation and $A^-$ is an anion of formula $[N(R_f)_2]^-$, wherein $R_f$ is a partially or fully fluorine-substituted alkyl having 1 to 8 C atoms or $R_{f2}X$, wherein $R_{f2}$ is a partially or fully fluorine-substituted alkyl having 1 to 8 C atoms and X is $SO_2$ or CO, or a fluoroalkylphosphate of formula $[PF_x(C_yF_{2y+1-z}H_{6-x})]^-$, wherein $1 \leq x < 6$, $1 \leq y \leq 8$ and $0 \leq z \leq 2y+1$;

or a mixture of said formulas.

2. A method according to claim 1, wherein the biological sample comprises tissues, cells, cell cultures and/or body fluids, or a mixture thereof.

3. A method according to claim 1, wherein the biological sample is fixed.

4. A method according to claim 3, wherein the biological sample is fixed using formalin.

5. A method according to claim 1, wherein the extraction is carried out at a temperature from between 0° C. to 95° C.

6. A method according to claim 1, wherein $A^-$ is an anion of formula $[N(R_f)_2]^-$, wherein $R_f$ is trifluoromethyl, pentafluoroethyl, nonafluorobutyl or $R_{f2}SO_2$.

7. A method according to claim 1, wherein $A^-$ is an anion of formula $[N(R_f)_2]^-$, wherein $R_f$ is trifluoromethyl.

8. A method according to claim 1, wherein $A^-$ is an anion of formula $[N(R_f)_2]^-$, wherein $R_f$ is as defined in claim 1 and X is a fluoroalkylphosphate of formula $[PF_3(C_yF_{2y+1})_3]^-$, wherein y=2, 3, or 4;

or a mixture of said formulas.

\* \* \* \* \*